(12) United States Patent
Hiramoto et al.

(10) Patent No.: US 7,193,227 B2
(45) Date of Patent: Mar. 20, 2007

(54) ION BEAM THERAPY SYSTEM AND ITS COUCH POSITIONING METHOD

(75) Inventors: Kazuo Hiramoto, Hitachiohta (JP); Hiroshi Akiyama, Hitachiohta (JP); Yoshihiko Nagamine, Hitachi (JP); Alfred Smith, Houston, TX (US); Wayne Newhauser, Houston, TX (US)

(73) Assignees: Hitachi, Ltd., Tokyo (JP); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/039,959

(22) Filed: Jan. 24, 2005

(65) Prior Publication Data

US 2006/0163495 A1 Jul. 27, 2006

(51) Int. Cl.
*A61N 5/01* (2006.01)
*A61N 5/10* (2006.01)

(52) U.S. Cl. ............... 250/492.3; 250/492.1; 250/492.21; 250/492.23; 378/4; 378/21; 378/29; 378/62; 378/63; 378/64; 378/65; 378/208; 378/209

(58) Field of Classification Search .............. 250/492.3
See application file for complete search history.

(56) References Cited

U.S. PATENT DOCUMENTS

| | | | |
|---|---|---|---|
| 5,039,867 A | 8/1991 | Nishihara et al. | |
| 5,207,223 A * | 5/1993 | Adler | 600/427 |
| 5,825,845 A * | 10/1998 | Blair et al. | 378/62 |
| 5,993,373 A | 11/1999 | Nonaka et al. | |
| 6,094,760 A | 8/2000 | Nonaka et al. | |
| 6,307,914 B1 * | 10/2001 | Kunieda et al. | 378/65 |
| 6,560,354 B1 * | 5/2003 | Maurer et al. | 382/131 |
| 2004/0184583 A1 * | 9/2004 | Nagamine et al. | 378/209 |
| 2005/0051740 A1 * | 3/2005 | Yanagisawa et al. | 250/492.1 |
| 2006/0163495 A1 * | 7/2006 | Hiramoto et al. | 250/492.3 |

(Continued)

FOREIGN PATENT DOCUMENTS

JP 1-151467 6/1989

(Continued)

*Primary Examiner*—Nikita Wells
*Assistant Examiner*—Bernard Souw
(74) *Attorney, Agent, or Firm*—Dickstein Shapiro LLP

(57) ABSTRACT

A therapy system using an ion beam, which can shorten the time required for positioning a couch (patient). The therapy system using the ion beam comprises a rotating gantry provided with an ion beam delivery unit including an X-ray tube. An X-ray detecting device having a plurality of X-ray detectors can be moved in the direction of a rotation axis of the rotating gantry. A couch on which a patient is lying is moved until a tumor substantially reaches an extension of an ion beam path in the irradiating unit. The X-ray tube is positioned on the ion beam path and the X-ray detecting device is positioned on the extension of the ion beam path. With rotation of the rotating gantry, both the X-ray tube emitting an X-ray and the X-ray detecting device revolve around the patient. The X-ray is emitted to the patient and detected by the X-ray detectors after penetrating the patient. Tomographic information of the patient is formed based on signals outputted from the X-ray detectors. Information for positioning the couch is generated by using the tomographic information.

26 Claims, 7 Drawing Sheets

U.S. PATENT DOCUMENTS

2006/0192072 A1* 8/2006 Yamashita et al. .......... 248/664

FOREIGN PATENT DOCUMENTS

| JP | 1-209077 | 8/1989 |
| JP | 11-47287 | 2/1999 |
| JP | 11-313900 | 11/1999 |
| JP | 2000-510023 | 8/2000 |

* cited by examiner

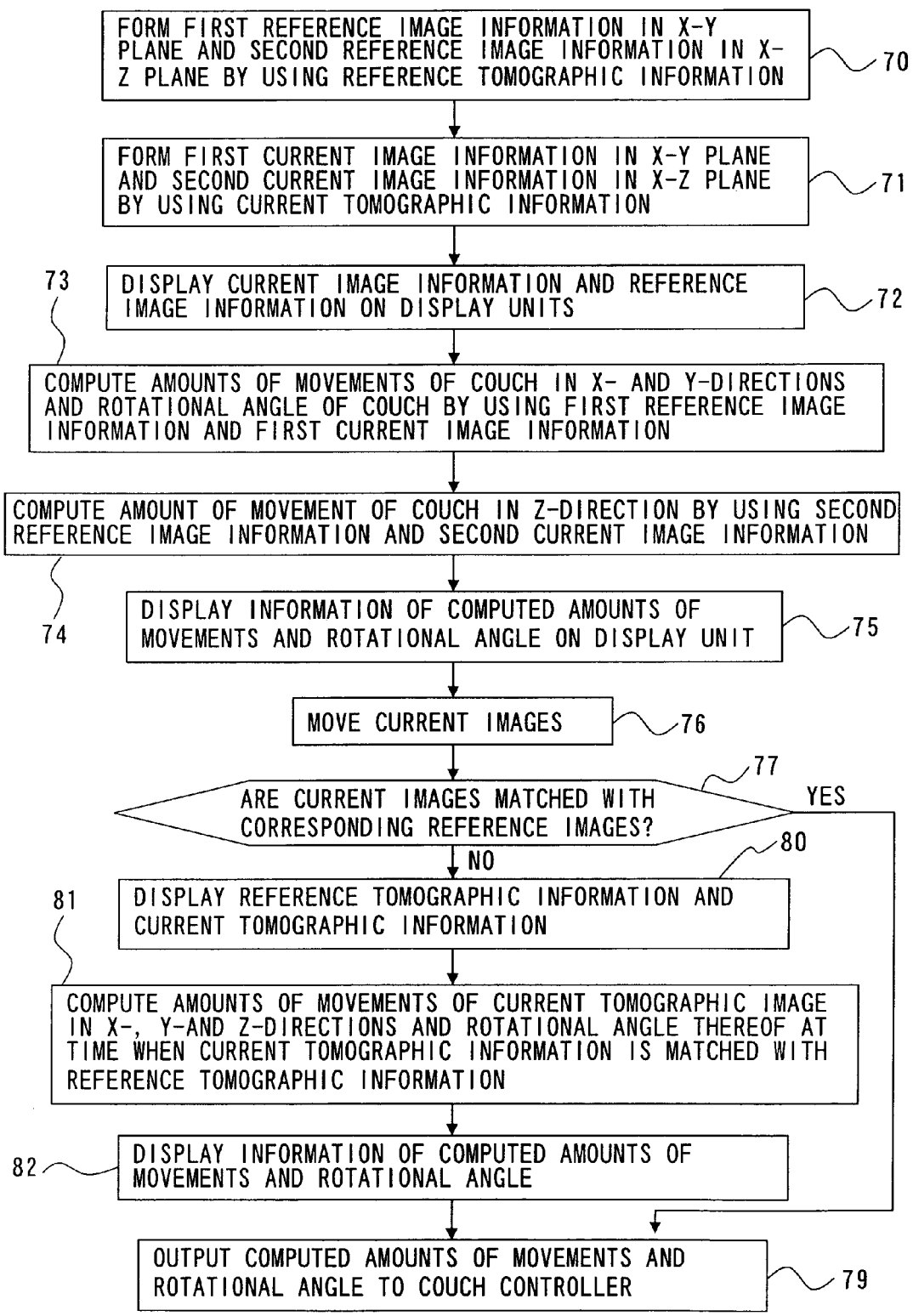

ION BEAM THERAPY SYSTEM AND ITS COUCH POSITIONING METHOD

BACKGROUND OF THE INVENTION

1. Field of the Invention

The present invention relates to a therapy system using a radiation and a method of positioning a patient couch. More particularly, the present invention relates a therapy system using an ion beam, such as a proton or a carbon ion beam, to a tumor (diseased tissue) for treatment, and a couch positioning method.

2. Description of the Related Art

There is known a therapy method of setting an irradiation target center at a tumor, e.g., a cancer, in a patient's body and delivering an ion beam, such as a proton or carbon ion beam, to the tumor. An ion beam therapy system with such a therapy method comprises a beam generator consisting of an accelerator and a beam transport system, and a beam delivery unit mounted to a rotating gantry. Ion beam accelerated by the accelerator reaches the beam delivery unit through the beam transport system, and is monitored and shaped to conform to the shape of the tumor in the patient's body by the beam delivery unit. Ion beam, such as a proton or carbon ion beam, has a characteristic that most of beam energy is released just before the particles of the beam come to rest (The resulting shape of the radiation dose distribution is called a "Bragg peak"). In the particle beam therapy system, kinetic energy of the ion beam is selected so that the ion beam may stop in the irradiation target and deposit most of the its energy to the tumor based on the above-mentioned characteristic.

Prior to irradiation with an ion beam, the tumor must be properly positioned with respect to the beam delivery unit so that the tumor irradiation dose is maximized at the tumor and the damage to normal tissues is minimized.

For that reason, a patient couch is positioned by a patient couch positioning apparatus (see, e.g., U.S. Pat. No. 5,825,845 (JP, A 2000-510023)). In order to accurately position the patient relative to the beam delivery unit by use of the patient couch positioning apparatus, the position of the irradiation target is decided beforehand relative to particular localization points in the patient's body (e.g. bony landmarks) by using two orthogonal display images.

Prior to the irradiation with an ion beam, an X-ray source is inserted into the location of the ion beam path within the beam delivery unit, and an X-ray image receptor (a plurality of X-ray detectors) is inserted on an extension of the beam path on the opposite side of the patient lying on the couch. The X-ray image receptor produces a radiographic transmission image of the patient's body. To align the tumor with the isocenter located on the extension of the beam path, the direction in and the distance by which the patient couch is to be moved relative to the beam delivery unit are determined by using the offset distance on the X-ray image from each of the particular localization points to the center of the X-ray beam and the offset distance on the DRR from the same particular monument to the isocenter. Then, the patient is repositioned using positioning control of the patient couch, based on the thus-determined direction and distance of movement of the patient couch.

A process of computing the direction and the amount of movement of a couch to position the tumor relative to a beam delivery unit for an ion beam by using a control image (reference image) formed from a tomographic image obtained by X-ray CT (computerized tomography) beforehand (before the positioning procedure) and current orthogonal X-ray images obtained by an X-ray source and an X-ray image receptor is described in from line 37, column 8 to line 66, column 9 (particularly (1a)–(1h)) and FIGS. 3, 4 and 5 of U.S. Pat. No. 5,039,867 (JP,A 1-151467 and JP,A 1-209077). Also, a process of positioning one X-ray CT unit below a vertical beam delivery unit so as to position on a beam axis of the beam delivery unit and computing the amount of movement of a couch by using a tomographic image (current tomographic image) obtained by the one X-ray CT unit and a tomographic image (reference tomographic image) obtained by another X-ray CT unit before decision of a treatment plan is described from line 67, column 9 to line 18, column 11 (in particular (2a)–(2g)) and FIG. 6 of U.S. Pat. No. 5,039,867.

SUMMARY OF THE INVENTION

With the positioning process described in U.S. Pat. No. 5,825,845 and from line 37, column 8 to line 66, column 9 of U.S. Pat. No. 5,039,867, the position of the X-ray source is held in one point at the time of X-ray emission, and the X-ray image is formed with the X-ray beam emitted from the fixed (but it is retractable) X-ray source and having passed through the tumor in the patient's body. It has been, therefore, not easy to obtain clear and accurate information regarding the shape and position of the tumor in the patient's body (hereinafter referred to simply as "position information") which is three-dimensional in nature.

On the other hand, with the positioning process described in from line 67, column 9 to line 18, column 11 of U.S. Pat. No. 5,039,867, a three-dimensional current tomographic image including the tumor can be formed by employing the X-ray CT technique. In comparison with the positioning process using the X-ray image described in U.S. Pat. No. 5,825,845, therefore, the couch can be positioned at higher accuracy by using the current tomographic image and the reference tomographic image.

It is sometimes necessary to combine the rotation of the beam delivery unit with positioning the couch in the horizontal direction, disclosed in FIGS. 1, 2 and 11 of U.S. Pat. No. 6,094,760(JP, A 11-313900) so that the direction of irradiation of the ion beam with respect to the tumor can be more freely set. In the case of employing the beam delivery unit mounted to the rotating gantry to accomplish such a goal, however, because the couch is positioned by using a temporarily moved X-ray CT unit and a current tomographic image obtained by the X-ray CT unit as disclosed in U.S. Pat. No. 5,039,867, the time required for positioning the couch is prolonged and the treatment time per patient is increased. More specifically, a couch used in a particle beam therapy system, on which the patient is lying, is moved in the X-, Y- and Z-directions and further rotated in the horizontal direction by a moving apparatus disclosed in U.S. Pat. No. 6,094,760. Then, while keeping the position of the couch as it is, an X-ray CT unit is moved to a position on an extension of the beam path of the beam delivery unit where a current tomographic image including the tumor is then obtained. At this time, the couch is located in the X-ray CT unit. After the end of image acquisition by the X-ray CT unit, the X-ray CT unit is moved away from the beam delivery unit to a position out of interference with the irradiation of an ion beam. Those movements for setting and retracting the X-ray CT unit increase the time required for positioning the couch. It is difficult and takes a longer time, in particular, to move the X-ray CT unit without moving the couch such that the couch is located in the X-ray CT unit and the X-ray CT unit is moved to the position on the extension of the beam path.

Furthermore, since the isocenter of the X-ray CT does not necessarily coincide with that of the rotating gantry, it is necessary that the image obtained by the X-ray CT is transformed to that in the coordinate around the isocenter of the rotating gantry. This also extends the time for the preparation of the treatment for a patient.

Accordingly, it is an objective of the present invention to provide a therapy system using an ion beam, and a couch positioning method, which can reduce the time required for positioning a patient couch in order to achieve an accurate positioning of the target volume within the therapeutic radiation field.

To achieve the above goal, the present therapy system has a rotational gantry not only for the traditional therapy purposes using the ion beam but also for obtaining 3-dimensional imaging information that yields accurate positioning information for locating the patient couch. The present rotating gantry, which is provided with a beam delivery unit for delivering ion beam to a tumor in treatment, includes a X-ray generator, which is capable of moving to a position of a radiation path of the ion beam radiation and revolving about a rotation axis of the rotating gantry with rotation of the rotating gantry and generates X-ray at a plurality or rotating angles of the rotating gantry, and also includes a X-ray detection unit (a plurality of X-ray detectors), which detects the X-ray emitted from the X-ray generator, outputs X-ray detection signals and revolves about the rotation axis of the rotating gantry with rotation of the rotating gantry.

With the present invention, both the X-ray generator and X-ray detection unit mounted to the rotating gantry are operated at various rotating angles of the rotating gantry, and three dimensional tomographic information of the irradiation target is formed by using information obtained based on the X-ray detection signals outputted respectively from the X-ray detection unit, there is no need of moving an X-ray CT unit for positioning the couch to the position of the radiation path and retreating the X-ray CT unit to a position out of interference with irradiation of the first radiation to the irradiation target after capturing an X-ray CT image. There is also no need for the transformation of the radiographic image or the irradiation target's coordinate which was necessary in the case using the above separate X-ray CT unit. As a result, the time required for positioning the couch can be cut down and the accuracy of positioning the tumor increased.

Preferably, the X-ray generator is provided in the beam delivery unit and is movable between a first position lying in the radiation path and a second position away from the radiation path. With this feature, the X-ray generator can be easily moved between the first position and the second position, and a structure for mounting the X-ray generator to the rotating gantry can be simplified.

Preferably, the therapy system further comprises a positioning information generator for generating information for positioning the couch by using the first tomographic information and second tomographic information of the irradiation target used in a treatment plan for the irradiation target, and a couch movement controller for controlling movement of the couch by using the positioning information. With this feature, positioning of the couch can be controlled by the couch controller in accordance with information generated from the positioning information generator.

Hence, according to the present invention, it is possible to reduce the time required for positioning the couch (patient) in order to align the tumor with the therapeutic radiation field while simultaneously increase the accuracy of the positioning.

BRIEF DESCRIPTION OF THE DRAWINGS

FIG. 11 is a flowchart showing still another example of the processing sequence executed by the positioning data generator to compute amounts of movements of the couch.

DESCRIPTION OF THE PREFERRED EMBODIMENTS

Figure 1:
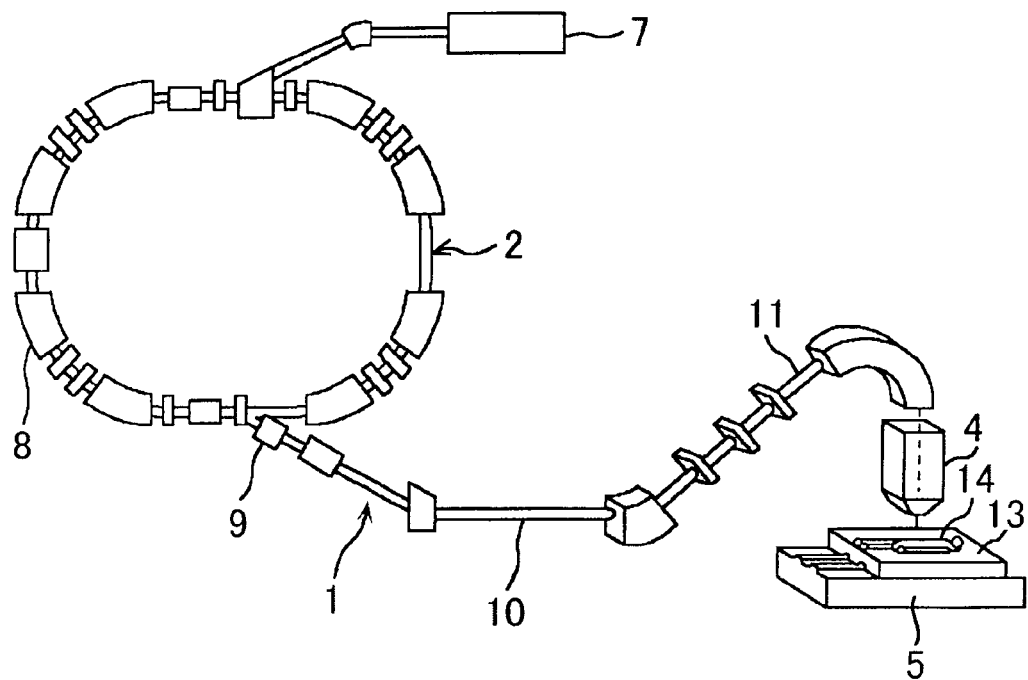
FIG. 1 is a schematic view of a therapy system according to an embodiment of the present invention.
Figure 2:
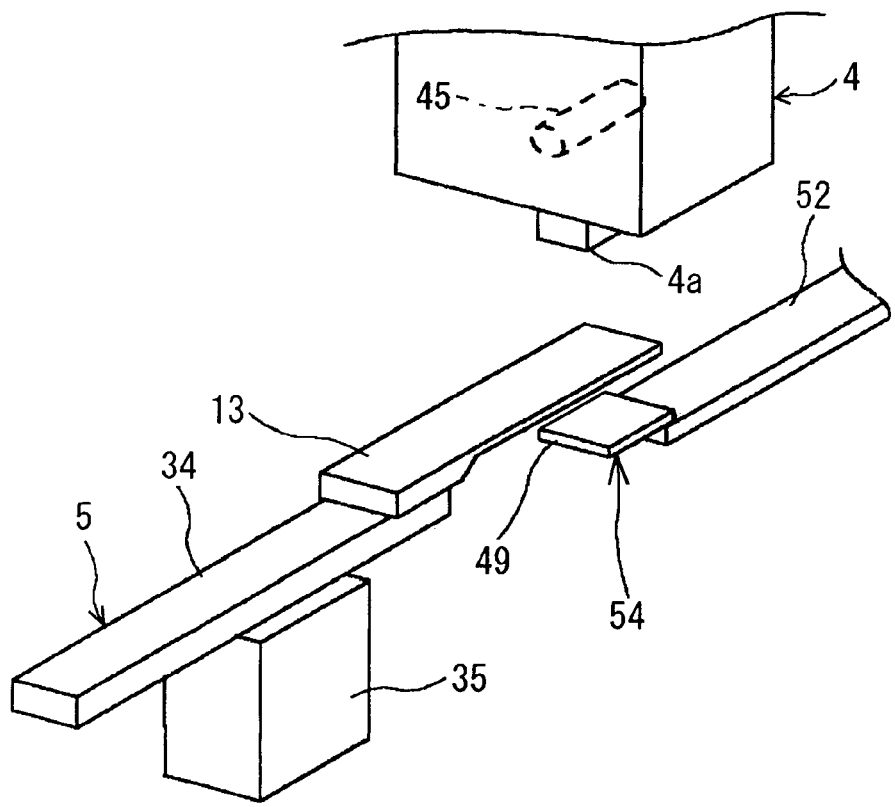
FIG. 2 is an explanatory view for explaining the positional relationship between an X-ray tube and an X-ray image receiving system at the time of taking X-ray CT pictures.

A radiation therapy system according to one preferable embodiment of the present invention will be described below with reference to FIGS. 1 to 11. A therapy system 1 constituting the radiation therapy system of this embodiment comprises a beam generator 2, a rotating gantry 3 (see FIG. 3), a beam delivery unit 4, a treatment bench 5 (see FIG. 2), and a couch positioning apparatus 6 (see FIG. 5). The couch positioning apparatus 6 comprises an X-ray source device (X-ray generator) 39, an image receiving system 40, an X-ray source controller 41, and an image receptor movement controller 42. The radiation therapy system of this embodiment is a cancer treatment system. The beam generator 2 comprises an ion source (not shown), a pre-stage accelerator 7, and a synchrotron 8. Ions (e.g., proton ions or carbon ions) generated from the ion source are accelerated by the pre-stage accelerator (e.g., a linear accelerator) 7. A resulting ion beam (e.g., a proton beam) enters the synchrotron 8 from the pre-stage accelerator 7. In this embodiment, a proton beam is employed as the ion beam. The ion beam is accelerated in the synchrotron 8. After the energy of the ion beam has been increased up to a preset level of energy, the ion beam is extracted from the synchrotron 8 through an extraction deflector 9.

The ion beam having been extracted from the synchrotron 8 reaches, through a beam transport system 10, a beam delivery unit 4 serving as an apparatus for delivering the ion beam to the patient. The beam delivery unit 4 and an inverted U-shaped beam transport subsystem 11, which is a part of the beam transport system 10, are mounted to the rotating gantry 3 (see FIG. 3) and are rotated with the rotating gantry 3. The ion beam is delivered to a tumor (diseased part) 15 (see FIG. 8) in the body of a patient 14, who is lying on a treatment couch (hereinafter also referred to simply as a "couch") 13 as a part of the treatment bench 5, from an exit 4a of the beam delivery unit 4 through the beam transport subsystem 11.

Figure 3:
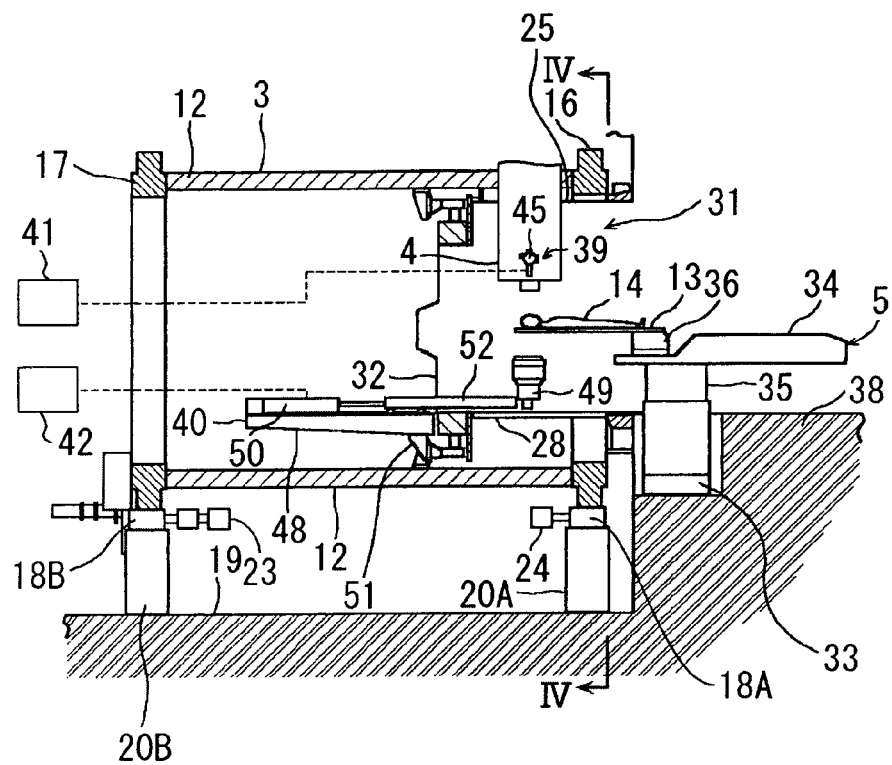
FIG. 3 is a vertical sectional view of a cylindrical rotating drum of a rotating gantry provided with an X-ray source unit and the X-ray image receptor (a plurality of X-ray detectors) in the particle beam therapy system shown in FIG. 1.

As shown in FIG. 3, the rotating gantry 3 includes a cylindrical rotating drum (rotating body) 12 having a front ring 16 and a rear ring 17. The front ring 16 provided at one end of the rotating drum 12 is supported by a plurality of rotational support rollers 18A. The support rollers 18A are mounted to roll support members 21 of a support unit 20A installed in a rotating gantry installation area (building base) 19 (see FIG. 4). The rear ring 17 provided at the other end of the rotating drum 12 and having an outer diameter equal to that of the front ring 16 is similarly supported by a plurality of support rollers 18B which are rotationally mounted to roll support members (not shown) of a support unit 20B. A first motor 23 is coupled to a rotary shaft for one of the plurality of support rollers 18B. In this connection, a rotational angle of the rotating gantry 3 is measured by an angle sensor 24 coupled to a rotary shaft for one of the plurality of support rollers 18A supporting the front ring 16.

An irradiation chamber 25 for particle beam treatment is formed inside the rotating drum 12. A schematic structure of the irradiation chamber 25 for particle beam treatment will be described below with reference to FIGS. 3 and 4.

Figure 6:
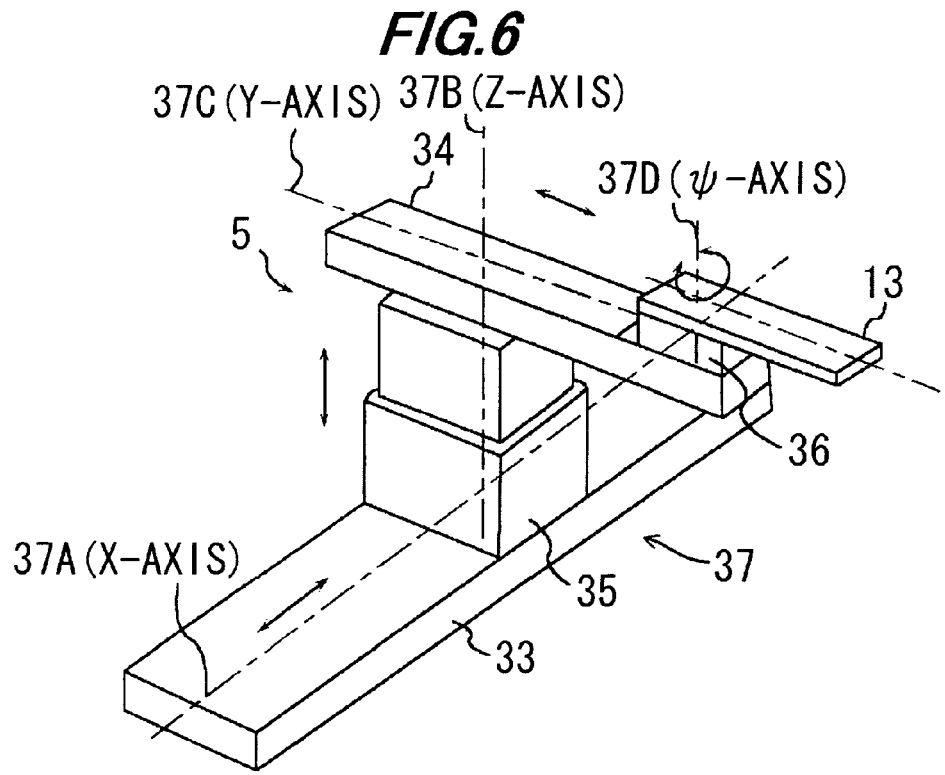
FIG. 6 is a perspective view of a treatment bench in the particle beam therapy system shown in FIG. 1.

As shown in FIG. 6, the treatment bench 5 includes a couch driver 37 comprising the couch 13, an X-direction driving mechanism 33, a Y-direction driving mechanism 34, a vertical driving mechanism 35, and a rotation driving mechanism 36. The X-direction driving mechanism 33 is installed in a treatment bench mount area 38. The X-direction driving mechanism 33 and the vertical driving mechanism 35 are both disposed outside the rotating drum 12. The vertical driving mechanism 35 is mounted on the X-direction driving mechanism 33, and the Y-direction driving mechanism 34 is mounted on the vertical driving mechanism 35. The couch 13 is mounted on the rotation driving mechanism 36 and supported by the couch driver 37.

The couch 13 is moved by the X-direction driving mechanism 33 in the direction of an articulation axis 37A (X-axis) that is horizontally extended parallel to the front ring 16. Also, the treatment couch 13 is moved by the vertical driving mechanism 35 in the direction of the articulation axis 37B (Z-axis) that is perpendicular to the articulation axis 37A. Further, the treatment couch 13 is moved by the Y-direction driving mechanism 34 in the direction of the articulation axis 37C (Y-axis) that is perpendicular to both the articulation axis 37A (X-axis) and the articulation axis 37B (Z-axis) and is extended in the direction of a rotation axis of the rotating drum 12. In other words, the treatment couch 13 is moved into and out of the treatment cage 31 by the Y-direction driving mechanism 34. Furthermore, the treatment couch 13 is rotated by the rotation driving mechanism 36 about an articulation axis 37D (ψ-axis) that is perpendicular to the articulation axis 37C (Y-axis).

The construction of the couch positioning apparatus 6 will be described with reference to FIGS. 3 to 5. As shown in FIG. 3, the couch positioning apparatus 6 comprises an X-ray source device (X-ray generator) 39, an image receiving system 40, an X-ray source controller 41, and an image receptor movement controller 42. Additionally, the X-ray source device 39 is housed in the beam delivery unit 4, and the image receiving system 40 is fixed to the inner surface of the rotating drum 12.

Figure 7A:
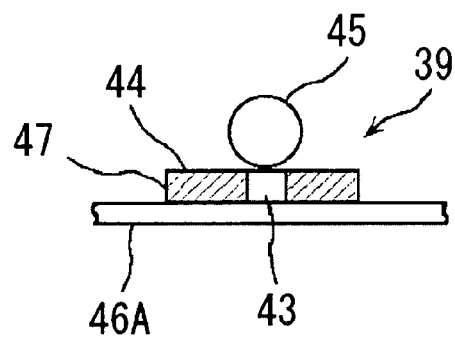
FIG. 7A is a schematic vertical sectional view of the X-ray source unit provided in a beam delivery unit shown in FIG. 1.
Figure 7B:
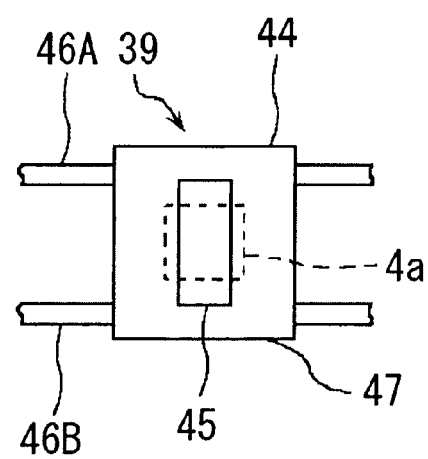
FIG. 7B is a plan view of the X-ray source unit shown in FIG. 7A.

As shown in FIGS. 7A and 7B, the X-ray source device 39 comprises a carriage 44 having an opening 43 formed in it, and an X-ray tube 45. The carriage 44 moves on guide rails 46A, 46B installed in the beam delivery unit 4. An X-ray source moving device 47 is constituted by the carriage 44 and a second motor (not shown) mounted on the carriage 44. With driving of the second motor, the carriage 44 is moved, thereby causing the X-ray tube 45 to move between a first position where it lies on a central axis of an ion beam path (hereinafter referred to as a "beam axis") in the beam delivery unit 4 and a second position where it is away from the ion beam path. The X-ray tube 45 illustrated in FIG. 4 is located at the first position. The image receiving system 40 comprises a guide member 48, a (radiographic) image receptor 49, and an image receptor moving device 50. The guide member 48 is positioned and extended in the axial direction of the rotating drum 12, and has one end fixed by a support member 51 to the inner surface of the rotating drum 12. An image receptor holding member 52 is mounted to one surface of the guide member 48. The image receptor moving device 50 is fixed to the one surface of the guide member 48 and is also coupled to the image receptor holding member 52. The image receptor moving device 50 includes the image receptor holding member 52. The image receiving system 40 and the X-ray source device 39 (or the beam delivery unit 4) thus constructed are arranged in a relation opposed to each other with the rotation axis of the rotating drum 12 between them.

Figure 4:
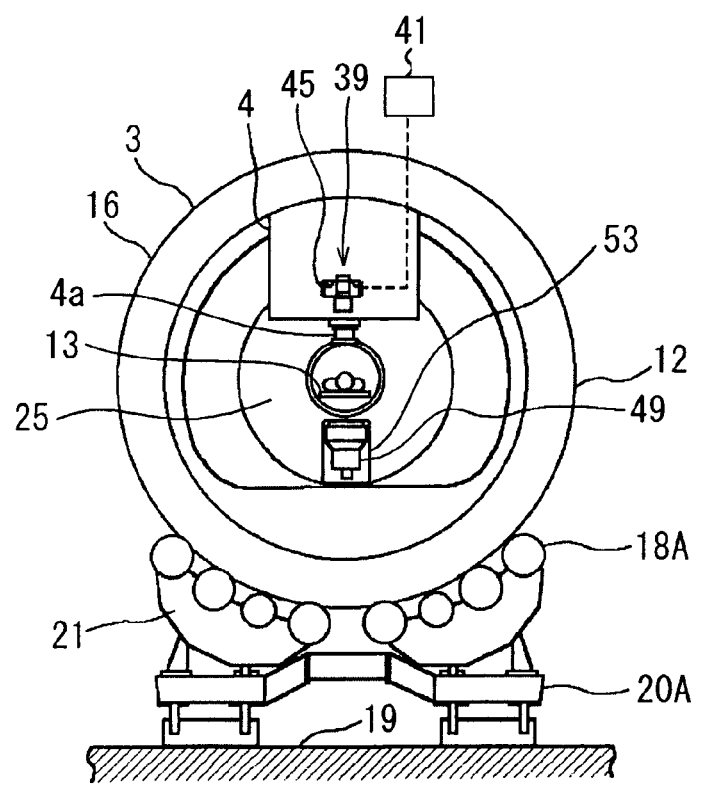
FIG. 4 is a view of the rotating gantry taken along the line IV—IV in FIG. 3, looking in the direction of arrows.

An opening 53 is formed in the partition 32 and is arranged so as to surround the rotation axis of the rotating drum 12 (see FIG. 4). As shown in FIG. 4, the image receptor holding member 52 and the image receptor 49 of the image receiving system 40 are movable into the treatment cage 31 while passing the opening 53.

The detailed construction of an X-ray image receiving system 54 will be described below with reference to FIG. 5. The X-ray image receiving system 54 comprises an X-ray detecting device (radiation detecting device) 55, a plurality of signal amplifiers 56, a plurality of signal processing units 57, and an image information forming unit (tomographic information forming unit) 58. The X-ray detecting device 55 is installed on a support member (not shown) for the image receptor 49. The X-ray detecting device 55 has a plurality of X-ray detectors 59 such as scintillators or semiconductors for detecting an X-ray, which are arranged in a closely adjacent state such that, looking from the beam delivery unit 4, they lie on one line as viewed in the X-direction (i.e., as viewed in the direction perpendicular to the drawing sheet of FIG. 5) and they are spaced at short intervals in the Y-direction (i.e., along the rotation axis of the rotating drum 12 or in the vertical direction in FIG. 5). An X-ray incident surface of each detector 59, which is positioned to face the beam delivery unit 4, has a square shape with one side of about 1.5 mm, for example. The plurality of detectors 59 are arranged in the Y-direction in a close relation to each other over a width of 50 cm, for example, so as to cover a maximum size of the irradiation field. By way of example, about 330 detectors 59 are arranged in the Y-direction. The detectors 59 may be arranged in plural rows (e.g., 2 to 3 rows) in the X-direction. The signal amplifiers 56 and the signal processing units 57 are put in a one-to-one relation to the detectors 59 and are connected in series corresponding the detectors 59. Information of the X-ray intensity outputted from each signal processing units 57 is transmitted to the image information forming unit 58. The X-ray detecting device 55, the plurality of signal amplifiers 56, and the plurality of signal processing units 57 are installed in the image receptor 49, while the image information forming unit 58 is installed at a position (e.g., in a control room) away from the rotating gantry 3.

Figure 5:
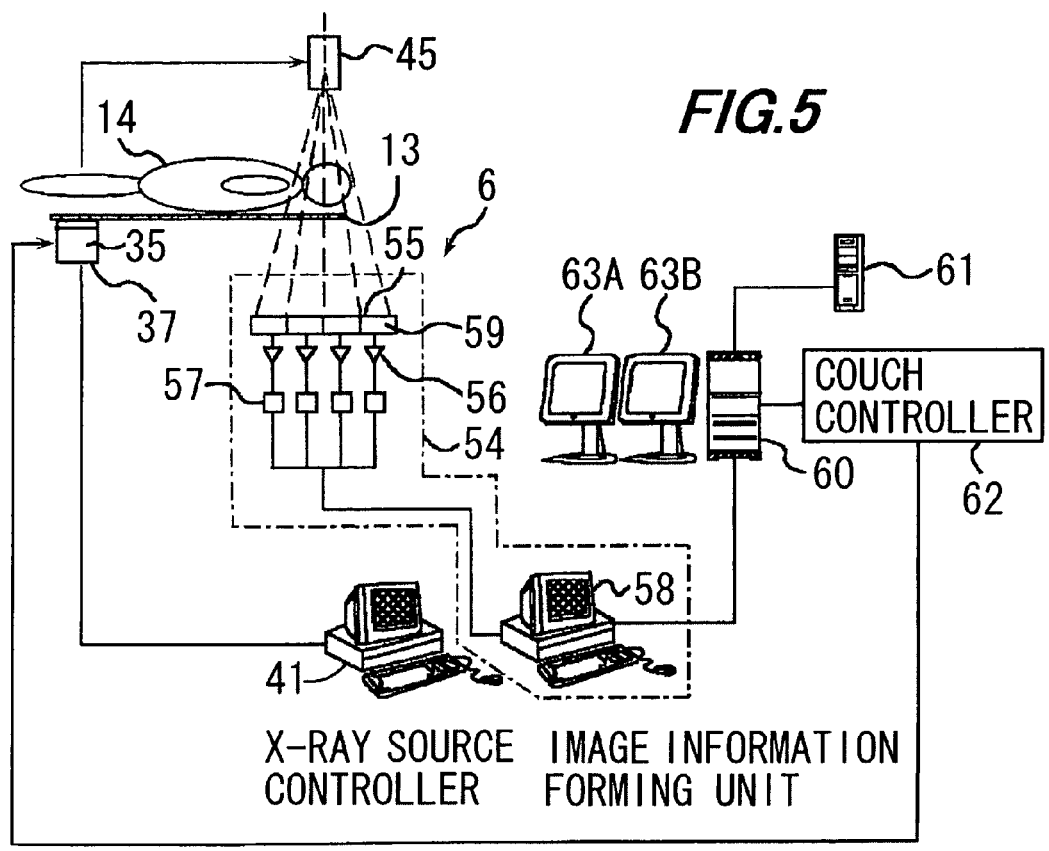
FIG. 5 is a schematic view of a couch positioning apparatus in the particle beam therapy system shown in FIG. 1.

In addition to the components described above, the couch positioning apparatus 6 further comprises, as shown in FIG. 5, a positioning data generator (processing unit) 60 having (not-shown) input means (such as a keyboard and a mouse), a medical image archive server 61, a couch controller 62, and display units 63A, 63B. The positioning data generator 60, the medical image archive server 61, the couch controller 62, and the display units 63A, 63B are all installed in the control room. The positioning data generator 60 is connected to the image information forming unit 58, the medical image archive server 61, the couch controller 62, and the display units 63A, 63B. A small-sized pendant (not shown) having an input device and a display unit is also provided such that it is transportable in the treatment cage 31 while being connected to the couch controller 62.

A manner of positioning the patient 14 (or the couch 13) in the radiation therapy system of this embodiment, having the above-described construction, will be described below.

First, an X-ray CT image is captured for the patient 14 on the treatment couch 13. The treatment couch 13 on which the patient 14 is lying is moved to a predetermined position within the treatment cage (treatment chamber) 31. This movement of the treatment couch 13 is performed under control of the couch controller 62. More specifically, an operator (e.g., a radiation therapist) in the treatment cage 31 is able to approximately know a treatment target position on the patient 14 (i.e., a position of the tumor 15 to which the ion beam is to be irradiated) based on treatment plan information displayed on the display unit (not shown) of the pendant. Thus, the operator inputs a treatment couch movement command to the couch controller 62 based on the treatment plan information by using the input device of the pendant. In accordance with the movement command, the couch controller 62 controls the couch driver 37, specifically driving the X-direction driving mechanism 33, the Y-direction driving mechanism 34, the vertical driving mechanism 35, and the rotation driving mechanism 36. As a result, the tumor 15 in the body of the patient 14 is moved to a position near not only the extension of the beam axis, but also a rotation axis (isocenter) 64 (see FIG. 8) of the rotating gantry 3. Additionally, the pendant is connected to the image receptor movement controller 42 and the X-ray source controller 41 as well.

Then, in order to move the image receptor 49 to a position opposed to the patient 15, the operator inputs a command for moving the image receptor 49 to the image receptor movement controller 42 from the pendant. Under control of the image receptor movement controller 42, the image receptor moving device 50 moves the image receptor holding member 52 along the guide member 48. With the movement of the image receptor holding member 48 through the opening 53, the image receptor 49 reaches a position below the couch 13 on the extension of the beam axis of the beam delivery unit 4. At this point, the operator stops inputting the movement command from the pendant. As a result, the X-ray detecting device 55 installed in the image receptor 49 is positioned below the tumor 15 in the body of the patient 14 lying on the couch 13. In other words, the X-ray detecting device 55, specifically the plurality of X-ray detectors 59, is located in a position where the X-ray detecting device 55 can receive an X-ray having penetrated the tumor 15.

Also, the operator inputs a command for moving the X-ray source device 39 to the X-ray source controller 41 from the pendant. Under control of the X-ray source controller 41 having received the movement command, the X-ray source moving device 47 moves the carriage 44 along the guide rails 46A, 46B together with the X-ray tube 45. As a result, the X-ray tube 45 is moved from the second position away from the beam path to reach the first position on the beam path within the beam delivery unit 4.

After rough position adjustment has been performed by the operator in such a way, an X-ray CT image is captured for the tumor 15 in the body of the patient 14 in a state where the patient 14 is positioned between the X-ray tube 45 and the X-ray detecting device 55 aligned in a spaced relation along the direction of propagation of the ion beam, while the rotating gantry 3 is rotated.

A more detailed description is now made of X-ray CT image capturing (hereinafter referred to as "current X-ray CT image capturing") by using the rotating gantry 3 in this embodiment. After the end of the rough position adjustment described above, the operator exits from the treatment cage 31 and enters the control room (not shown). Upon the operator manipulating an input device (not shown) provided on a console (not shown) installed in the control room, an X-ray irradiation command is outputted to the X-ray source controller 41, and a first gantry rotation command is outputted to a gantry controller (not shown).

Figure 8:
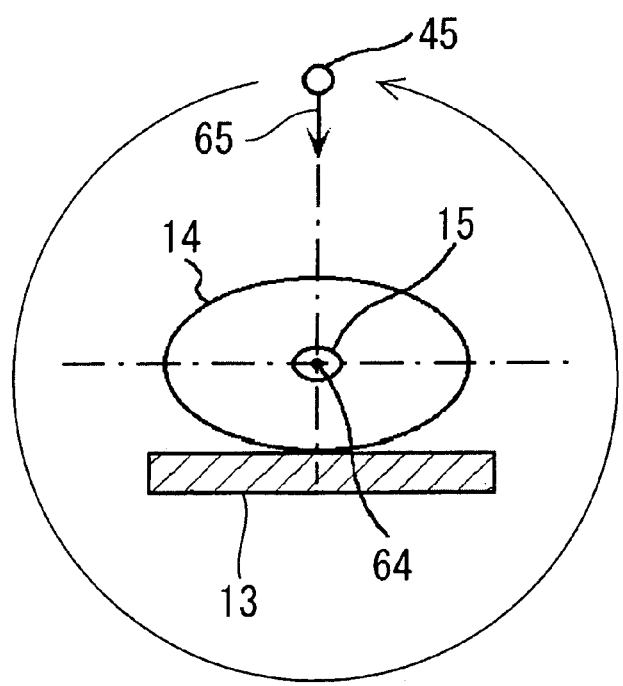
FIG. 8 is an explanatory view for explaining movement of the X-ray tube used at the time of emitting X-ray for taking CT pictures.

In accordance with the inputted X-ray irradiation command, the X-ray source controller 41 emits an X-ray 65 from the X-ray tube 45 toward the tumor 15 in the body of the patient 14 (see FIGS. 4 and 8). The X-ray 65 is emitted in a cone shape sized such that the X-ray is incident upon all or most of the detectors 59 arranged in a grid pattern over a square area with one side of 50 cm as described above. Also, in accordance with the inputted first gantry rotation command, the gantry controller drives the first motor 23. As a result, the rotating gantry 3 is rotated, whereby the beam delivery unit 4 including the X-ray tube 45 revolves around the couch 13 on which the patient 14 is lying (see FIG. 8). The rotational angle of the rotating gantry 3, i.e. of the rotating drum 12, is detected by the angle sensor 24. During the revolution of the beam delivery unit 4, the X-ray 65 is irradiated toward the patient 14 from the X-ray tube 45. After having penetrated the tumor 15 in the body of the patient 14, the X-ray 65 is detected by the detectors 59 of the X-ray detecting device 55 provided in the image receptor 49. The detectors 59 having detected the X-ray output respective X-ray detected signals (electric signals). The X-ray detected signals outputted from the detectors 59 are amplified by the corresponding signal amplifiers 56 and integrated by the corresponding signal processing units 57 at intervals of setting time. As a result of the integration, X-ray intensity information is obtained. The X-ray intensity information is inputted to the image information forming unit 58. When the rotating gantry 3 makes one rotation and the beam delivery unit 4 is returned to the start position, the driving of the first motor 23 is stopped in response to a rotation stop command inputted from the console to the gantry controller, whereupon the rotation of the rotating gantry 3 is stopped. Also, in response to an X-ray irradiation stop command inputted from the console to the X-ray source controller 41, the emission of the X-ray from the X-ray tube 45 is stopped. In the above-described process of capturing the X-ray CT image while rotating the rotating gantry 3, the time required for one rotation of the rotating gantry 3 is approximately one minute.

After the end of the current X-ray CT image capturing, the operator inputs an image receptor retract command from the console installed in the control room. In accordance with the image receptor retract command, the image receptor movement controller 42 drives the image receptor moving device 50 such that the image receptor 49 is moved to a position near the partition 32.

The image information forming unit 58 receives the X-ray intensity information from each signal processing unit 57 and the measured value of the rotational angle outputted from the rotating gantry angle sensor 24 shown in FIG. 3. Setting angle regions are set by dividing a circumference about the rotation axis of the cylindrical rotating drum 12 at intervals of a setting angle (e.g., 0.5 degree) in the rotating direction of the rotating drum 12. Those setting angle regions are stored in the image information forming unit 58. The setting angle may be set to any other suitable angle, e.g., 0.1 degree. Based on the inputted measured value of the rotational angle, the image information forming unit 58 recognizes each setting angle region in which the X-ray tube 45 is positioned during the rotation of the rotating gantry 3. This is equivalent to recognizing the position of the X-ray tube 45 in the circumferential direction of the cylindrical rotating drum 12. Once the position of the X-ray tube 45 is determined, the position of each detector 59 at that time, which is in an opposite position to the X-ray tube 45, is also determined. Then, the image information forming unit 58 determines a radiation attenuation factor between the X-ray tube 45 and each detector 59 by using the position information of the X-ray tube 45, the position information of each detector 59 corresponding to the position information of the X-ray tube 45, and the X-ray intensity information detected by each detector 59 at the relevant position. Further, based on the radiation attenuation factor, the image information forming unit 58 determines a radiation attenuation value for each small volume inside the patient by using, e.g., the so-called Filtered Back Projection Method described in IEEE Transaction on Nuclear Science, pp. 228–229, Vol. NS-21, and converts the determined value into a CT value. By using the CT value thus obtained, the image information forming unit 58 forms tomographic information (hereinafter referred to as "current tomographic information") including the tumor 15 in the body of the patient 14. Because the detectors 59 of about 330 are arranged in the axial direction of the rotating drum 12, it is possible to form three-dimensional current tomographic information covering the width of 50 cm in the axial direction of the rotating drum 12. The formed tomographic information is inputted to the positioning data generator 60.

Meanwhile, the medical image archive server 61 takes in, from a storage in a treatment planning unit (not shown), three-dimensional tomographic information (hereinafter referred to as "reference tomographic information") obtained by X-ray CT image capturing (hereinafter referred to as "reference X-ray CT image capturing) which has been performed on the patient 14 beforehand (prior to the decision of the treatment plan), followed by storing the reference tomographic information in it.

After the rotation of the rotating gantry 3 is stopped and the current X-ray CT image capturing is brought to an end, the operator enters the treatment cage 31 again and inputs a second gantry rotation command to the gantry controller by manipulating the pendant. In response to the second gantry rotation command, the gantry controller rotates the rotating gantry 3 by using angle information of the rotating gantry 3 (i.e., information regarding the direction of irradiation of the ion beam), which is one of treatment plan information for the patient under treatment, until the beam delivery unit 4 reaches a predetermined angle. The processing in the image information forming unit 58 to form the current tomographic information is executed in parallel to the operation for rotating the rotating gantry 3.

By using the current tomographic information and the reference tomographic information, the positioning data generator 60 forms positioning data (first positioning data) in an X-Y plane (i.e., a plane defined by two X- and Y-direction axes) and positioning data (second positioning data) in an X-Z plane (i.e., a plane defined by two X- and Z-direction axes). A process of forming those positioning data will be described in more detail with reference to FIG. 9. First reference image information as two-dimensional image information in the X-Y plane (hereafter referred to as X-Y plane reference image information) including the isocenter (corresponding to the tumor) set in the treatment plan and second reference image information as two-dimensional image information in the X-Z plane (hereafter referred to as X-Z plane reference image information) including the isocenter are formed by using the reference tomographic information as three-dimensional image information (step 70). First current image information as two-dimensional image information in the X-Y plane (hereafter referred to as X-Y plane current image information), which is similar to the reference tomographic information, and second current image information as two-dimensional image information in the X-Z plane (hereafter referred to as X-Z plane current image information), which is similar to the reference tomographic information, are formed by using the current tomographic information as three-dimensional image information (step 71). When capturing the current X-ray CT image, the patient is fixed onto the couch by the same patient fixing fasteners as those used in the reference X-ray CT image capturing (which are also used when delivering the ion beam). It is therefore easy to form sectional image information as the current image information in the same section as the reference image information.

The X-Y plane current image information and the X-Y plane reference image information are outputted to the display unit 63A, and the X-Z plane current image information and the X-Z plane reference image information are outputted to the display unit 63B (step 72). Note that the X-Y plane and X-Z plane current image information corresponds to the X-TV images described in U.S. Pat. No. 5,039,867 (JP,A 1-209077), and the X-Y plane and X-Z plane reference image information corresponds to the control image described in U.S. Pat. No. 5,039,867 (JP,A 1-209077).

Then, the positioning data generator 60 computes the amounts of movements of the couch 13 in the X- and Y-axis directions and the rotational angle of the couch 13, which constitute the couch positioning data in the X-Y plane, by using the first current image information and the first reference image information (see FIG. 3 in U.S. Pat. No. 5,039, 867) (step 73). More specifically, as described in (1d), columns 8–9 of U.S. Pat. No. 5,039,867, the amounts of movements (shift amounts) of the couch 13 in the X- and Y-axis directions are computed by using land marks M1, M2 and M3 put on the first reference image and land marks N1, N2 and N3 put on the first current image at positions corresponding to land marks M1, M2 and M3. The rotational angle of the couch 13 about the $\psi$ axis is computed based on the positions of respective land marks contained in both the X-Y plane reference image information and the X-Y plane current image information.

The amount of movement of the couch 13 in the Z-axis direction, which constitutes the couch positioning data in the Z-X plane, is computed by using the X-Z plane current image information and the X-Z plane reference image information (step 74). The amount of movement of the couch 13 in the Z-axis direction is computed in a similar manner to that in step 73, as described in lines 51–58, column 9 of U.S. Pat. No. 5,039,867. The computed amounts of movements in the X-Y plane, and the computed amount of movement in the Z-X plane are outputted respectively to the display units 63A, 63B (step 75). The current image information is then moved (step 76). The X-Y plane current image information displayed on the display unit 63A is moved in accordance with the X-Y plane positioning data, and the X-Z plane current image information displayed on the display unit 63B is moved in accordance with the X-Z plane positioning data. While looking at both the display units, the operator inputs "YES" from an input device (not shown) at the time when the X-Y plane current image information is matched with the X-Y plane reference image information and the X-Z plane current image information is matched with the X-Z plane reference image information. If at least one of the match between the X-Y plane current and reference image information and the match between the X-Z plane current and reference image information is not achieved, the operator inputs "NO" from the input device. If "YES" is inputted, the positioning data generator 60 recognizes the match of and reference current image information with the corresponding first and second reference image information (step 76). Subsequently, the information of the amounts of movements and the rotational angle thus computed are outputted to the couch controller 62 (step 79).

If "NO" is inputted, the positioning data generator 60 recognizes that the match of the X-Y plane and X-Z plane current image information with the corresponding X-Y plane and X-Z plane reference image information is not achieved. In this case, processing of step 78 is executed. More specifically, the operator inputs "NO" and manipulates a mouse (not shown) so that the X-Y plane current image information is moved on a screen of the display unit 63A to be matched with the X-Y plane reference image information and the X-Z plane current image information is moved on a screen of the display unit 63B to be matched with the X-Z plane reference image information. In step 78, the respective amounts of movements of the couch 13 in the X-, Y- and Z-directions and the rotational angle of the couch 13 about the ψ axis are computed based on the respective movements of the X-Y plane and X-Z plane current image information. The information computed in step 78 is then outputted to the couch controller 62 (step 79).

The couch controller 62 controls the couch driver 37 to move the couch 13 in accordance with the respective amounts of movements of the couch 13 in the X-, Y- and Z-directions and the rotational angle of the couch 13 inputted to it. In other words, the X-direction driving mechanism 33 is driven in accordance with the amount of movement in the X-direction to move the couch 13 in the X-direction, and the Y-direction driving mechanism 34 is driven in accordance with the amount of movement in the Y-direction to move the couch 13 in the Y-direction. Further, the vertical driving mechanism 35 is driven in accordance with the amount of movement in the Z-direction to move the couch 13 in the Z-direction, and the rotation driving mechanism 36 is driven in accordance with the rotational angle to rotate the couch 13 about the ψ axis. With such driving of those driving mechanisms, the couch 13 is positioned relative to the beam delivery unit 4 so that the tumor 15 in the body of the patient 14 is matched with the beam axis of the beam delivery unit 4 and the rotation axis (i.e., the isocenter 64) of the rotating drum 12.

The data for positioning the couch 13 may be computed by a method comprising the steps of designating one or more points, each of which has two-dimensional coordinates, in each of the current image information and the reference image information displayed on the display units 63A, 63B, and carrying out Affine transformation of the first and second current image information so that a difference between the designated points is minimized. In this connection, for the purpose of enabling the operator to more easily visually recognize how the current image information and the reference image information are matched with each other, the current image information and the reference image information may be displayed on one display unit in a superposed relation.

After the positioning of the treatment couch 13 has been completed in such a way, the X-ray source moving device 47 moves the carriage 44 along the guide rails 46A, 46B together with the X-ray tube 45 under control of the X-ray source controller 41 having received the retract command, thereby causing the X-ray tube 45 to move from the first position to the second position within the beam delivery unit 4. Then, the iron beam exiting through the exit 4a of the beam delivery unit 4 is directed to the tumor 15 in the body of the patient 14 lying on the couch 13 positioned as described above.

This embodiment described above includes an X-ray CT apparatus, i.e., a tomographic image capturing apparatus, comprising the X-ray tube 45, the radiation detecting device 55, the rotating gantry 3, and the image information forming unit 58. With this embodiment, therefore, the current tomographic information used for positioning the couch can be obtained by the X-ray CT apparatus. This means that there is no need of using a separate X-ray CT unit so as to position on the extension of the ion beam path in the beam delivery unit 4 unlike the prior art described in from line 67, column 9 to line 18, column 11 and FIG. 6 of U.S. Pat. No. 5,039,867. Stated another way, this embodiment no longer requires a process of carrying the separate X-ray CT unit into the treatment gauge 31 from the treatment bench installation area 38, placing the X-ray CT unit on the movable floor 28 so as to position on the extension of the ion beam path in the beam delivery unit 4, and then carrying the X-ray CT unit out of the treatment gauge 31 to the treatment bench installation area 38 after the end of image capturing. Furthermore, there is no need of transforming the image and position information between the rotating gantry and the separate X-ray CT in the prior art. Accordingly, this embodiment results in reduction of the time required for positioning the couch, which will reach more than five minutes in comparison with the case of the prior art using a separate CT. The reduction of the time required for positioning the couch makes it possible to cut down the time during which each patient is bounded to the couch for treatment.

With this embodiment, an X-ray CT image can be easily captured by moving the X-ray tube 45 until reaching the ion beam path with the carriage 44 and by moving the radiation detecting device 55 until reaching the extension of the ion beam path with the image receptor moving device 50.

With this embodiment, since the couch 13 is positioned between the beam delivery unit 4 and the radiation detecting device 55, it is possible to greatly reduce a possibility that the X-ray tube 45 and the radiation detecting device 55 may interfere with the movement of the couch 13 in the step of positioning the couch.

With this embodiment, since the beam delivery unit 4 is utilized as a holding member for mounting the X-ray source device 39 to the rotating gantry 3, there is no need of additionally providing a separate holding member for mounting the X-ray source device 39 to the rotating gantry 3. This contributes to suppressing an increase of the weight of the rotating gantry 3 and further suppressing an increase of the capacity of the first motor 23 for rotating the rotating gantry 3. No need of additionally providing a separate holding member is also effective in simplifying the internal structure of the rotating gantry 3.

In the case of employing the prior art mentioned above and placing the X-ray CT unit on the movable floor 28, the thickness of the movable floor 28 must be increased to be endurable against the weight of the X-ray CT unit. With this embodiment, since there is no need of placing the X-ray CT unit on the movable floor 28, the thickness of the movable floor 28 can be reduced and the total weight of the movable floor 28 can be reduced. Consequently, the capacity of the first motor 23 can also be reduced.

In addition, with this embodiment, the X-ray tube 45 for emitting an X-ray used for positioning the couch and the image receptor 49 for receiving the positioning X-ray and outputting a corresponding output signal are both mounted to the rotating gantry 3, and an X-ray CT image is captured while rotating the rotating gantry 3. Projected image information is formed from thus-obtained tomographic information and is compared with projected image information obtained at the time when the treatment plan has been calculated, thereby locating the position of the tumor 15 in the body of the patient 14. Accordingly, as compared with the prior art in which two pairs of X-ray sources and X-ray receiving means are provided such that each pair of X-ray sources and X-ray receiving means are positioned in an opposite direction with the patient 14 and two X-ray beam paths are orthogonal to each other, and the position of the tumor 15 is located by using only two two-dimensional tumor images thus obtained, image information of the tumor 15 can be more precisely obtained because the position of the tumor 15 is located based on the tomographic information containing image information projected from various directions of rotation of the rotating gantry 3. As a result, unlike the prior art, it is no longer required to set an excessive margin for an irradiation region of the ion beam with respect to the actual tumor 15 for ensuring irradiation of the ion beam to the tumor 15 in its entirety. Hence, the ion beam can be accurately directed to only the tumor 15 and normal tissues can be protected against radiation damage.

Figure 10:
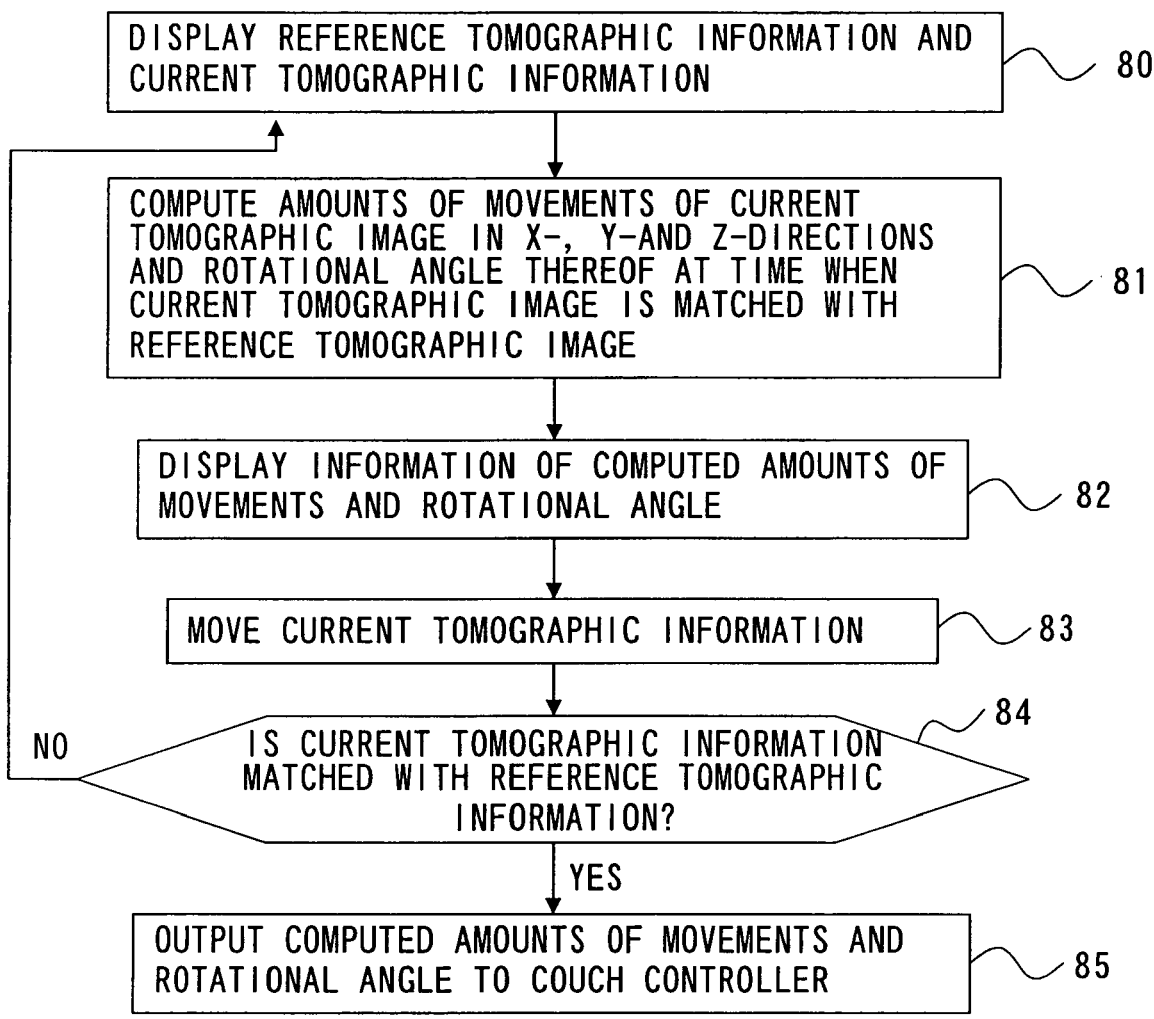
FIG. 10 is a flowchart showing another example of the processing sequence executed by the positioning data generator to compute amounts of movements of the couch.

Another example of the processing sequence executed by the positioning data generator 60 to compute the amounts of movements (shift amounts) of the couch 13 will be described below with reference to FIG. 10.

The positioning data generator 60 outputs to one display unit 63A, the reference tomographic information received from the medical image archive server 61 and the current tomographic information received from the image information forming unit 58 (step 80). The reference tomographic information and the current tomographic information are both displayed on the display unit 63A. Such three-dimensional image information can be displayed, for example, by a volume rendering display method for displaying three-dimensional image information as it is, or a surface display method for converting tomographic information into surface data through threshold processing.

The operator manipulates a mouse (not shown) so that a current tomographic image displayed on the screen of the display unit 63A is moved and matched with the reference tomographic image also displayed on it. In step 81, the respective amounts of movements of the couch 13 in the X-, Y- and Z-directions and the rotational angle of the couch 13 about the $\psi$ axis are computed based on the movement of the current tomographic image. The computed positioning data, i.e., the respective amounts of movements of the couch 13 in the X-, Y- and Z-directions and the rotational angle of the couch 13 about the $\psi$ axis, are displayed on the display unit 63A (or the display unit 63B) (step 82). Then, the positioning data generator 60 moves the current tomographic information (step 83). In other words, the current tomographic information displayed on the display unit 63A in the state corresponding to step 80 is moved in accordance with the obtained positioning data. While looking at the display unit 63A, the operator inputs "YES" from an input device (not shown) at the time when the current tomographic information is matched with the reference tomographic information. If the current tomographic information and the reference tomographic information are not matched with each other, the operator inputs "NO" from the input device. If "YES" is inputted, the positioning data generator 60 recognizes the match between the current tomographic information and the reference tomographic information (step 84). Subsequently, the information of the amounts of movements and the rotational angle thus computed are outputted to the couch controller 62 (step 85). If "NO" is inputted, the positioning data generator 60 recognizes that the current tomographic information and the reference tomographic information are not matched with each other, followed by repeating the processing of steps 81 to 84. If the match between the current tomographic information and the reference tomographic information is recognized in step 84, processing of step 85 is executed.

The couch controller 62 controls the couch driver 37 to position the couch 13 relative to the beam delivery unit 4, as described above, in accordance with the respective amounts of movements of the couch 13 in the X-, Y- and Z-directions and the rotational angle of the couch 13 inputted to it.

Instead of the above-described method of moving the tomographic images, the positioning data may be computed by a method comprising the steps of designating one or more points, each of which has three-dimensional coordinates, in each of the current tomographic information and the reference tomographic information displayed on the display units 63A, and carrying out Affine transformation of the current tomographic information so that a difference between the designated points is minimized.

With this example for computing the amounts of movements of the couch, the current tomographic information obtained by the current X-ray CT image capturing and the reference tomographic information obtained by the reference X-ray CT image are compared with each other to locate the position of the tumor 15 in the body of the patient 14. Thus, by using the current tomographic information and the reference tomographic information each being three-dimensional image information, it is possible to obtain highly accurate information for positioning the patient 15 (or the couch 13). The positioning information obtained with this example is more accurate than that obtained through the processing shown in FIG. 9, and therefore the accuracy in positioning of the couch 13 can be increased.

Figure 9:
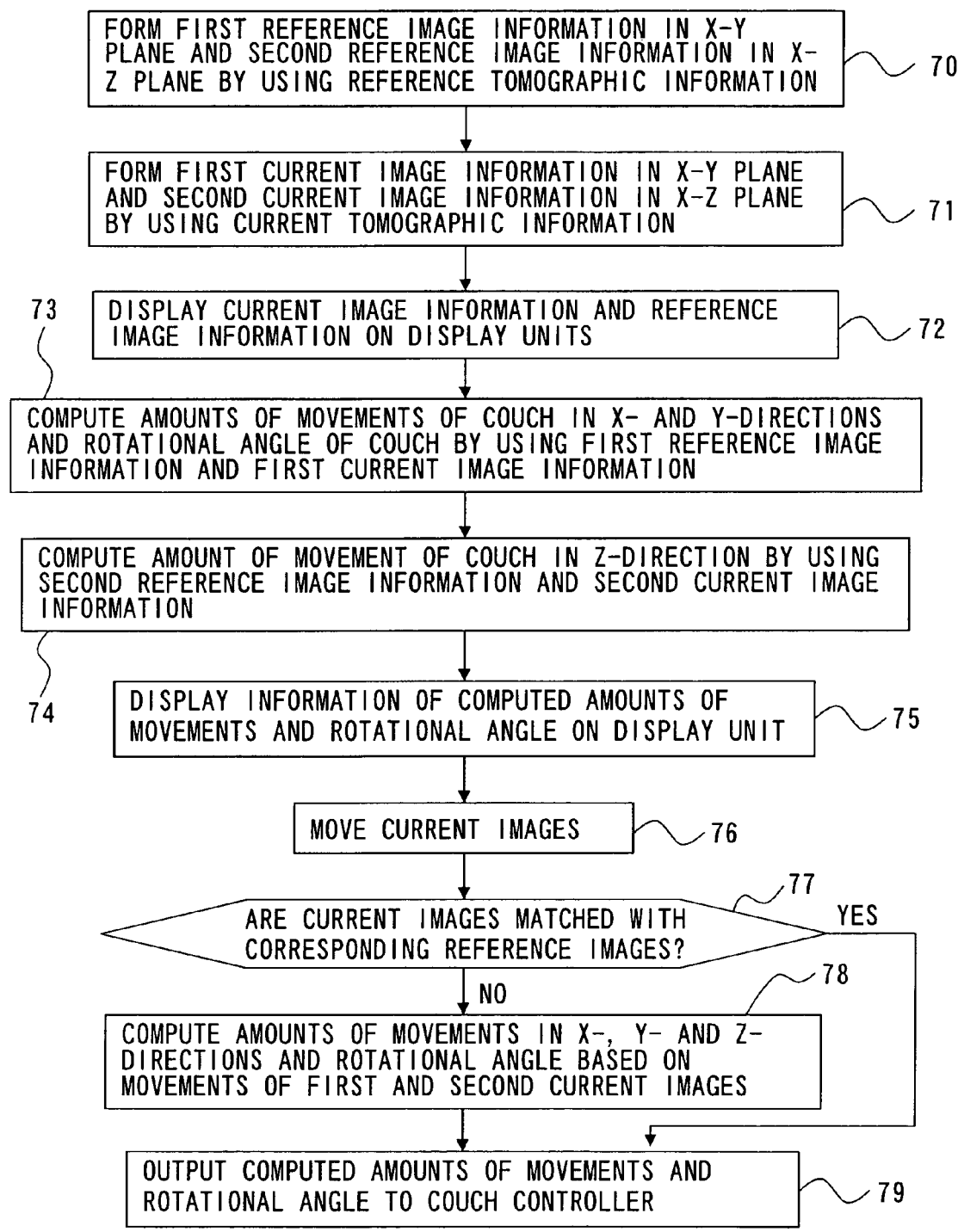
FIG. 9 is a flowchart showing one example of a processing sequence executed by a positioning data generator, shown in FIG. 5, to compute amounts of movements of a couch.

Still another example of the processing sequence executed by the positioning data generator 60 to compute the amounts of movements (shift amounts) of the couch 13 will be described below with reference to FIG. 11. In this example for computing the amounts of movements, the computing methods shown in FIGS. 9 and 10 are combined with each other. More specifically, the processing of steps 70 to 77 shown in FIG. 9 is executed. If the match of the X-Y plane and X-Z plane current image information with the corresponding X-Y plane and X-Z plane reference image information is recognized in step 76, the processing of step 79 is executed. If the match of the X-Y plane and X-Z plane current image information with the corresponding reference image information is not recognized in step 76, the processing of steps 80 to 82 shown in FIG. 10 is executed and the processing of step 79 is executed after step 82. In step 80, however, the current tomographic information is displayed on the display unit 63A together with the reference tomographic information such that the states of the X-Y plane and X-Z plane current image information after the movement thereof through the processing of step 76 are obtained. In step 81, the current tomographic information displayed in step 80 is matched with the reference tomographic information to obtain positioning information.

The couch controller 62 controls the couch driver 37 to position the couch 13 relative to the beam delivery unit 4, as described above, in accordance with the respective amounts of movements of the couch 13 in the X-, Y- and Z-directions and the rotational angle of the couch 13 inputted to it through the processing of step 79.

With this example, because of executing the processing of step 81, the positioning information can be obtained at higher accuracy than that obtained through the processing steps shown in FIG. 9. Also, since the positioning information is obtained by using the two-dimensional current image information and reference image information, the distance by which the three-dimensional current tomographic information is to be moved can be reduced, it is possible to reduce the capacity of data used for computing the amounts of movements of the couch based on the three-dimensional current tomographic information and reference tomographic information. As a result, the time required for obtaining the positioning information can be cut down in comparison with that obtained through the processing shown in FIG. 10.

What is claimed is:

1. A therapy system using an ion beam, in which an ion beam for treatment is delivered to an irradiation target, said therapy system comprising:
   a rotating gantry;
   a beam generator for generating said ion beam;
   a beam delivery unit mounted to said rotating gantry and delivering said ion beam;
   an X-ray generator generating an X-ray and mounted to said rotating gantry, said X-ray generator being capable of moving to a position of a beam path of said ion beam, revolving about a rotation axis of said rotating gantry with rotation of said rotating gantry and emitting X-ray at a plurality of rotation angles of said rotating gantry;
   a plurality of X-ray detectors for detecting the X-ray emitted from said X-ray generator and outputting X-ray detection signals, said plurality of X-ray detectors being mounted to said rotating gantry and revolving about the rotation axis of said rotating gantry with rotation of said rotating gantry; and
   an image information forming unit for forming three-dimensional image information of said irradiation target by using information obtained based on the X-ray detection signals from said plurality of X-ray detectors obtained upon rotation of said rotating gantry, position information of said X-ray generator emitting the X-ray and position information of said plurality of X-ray detectors outputting the X-ray detection signals.

2. A therapy system according to claim 1, wherein said X-ray generator is mounted in said beam delivery unit revolving about the rotation axis of said rotating gantry with the rotation of said rotating gantry, and is movable between a first position lying in said beam path and a second position away from said beam path.

3. A therapy system according to claim 1, wherein said beam delivery unit includes a moving device for moving said X-ray generator between said first position and said second position.

4. A therapy system according to claim 1, further comprising a couch capable of supporting said irradiation target and being positioned on an extension of said radiation path.

5. A therapy system according to claim 4, further comprising a positioning information generator for generating information for positioning said couch by using said three-dimensional image information and tomographic information of said irradiation target obtained at a treatment plan for said irradiation target, and a couch movement controller for controlling movement of said couch by using the positioning information.

6. A therapy system using an ion beam according to claim 2, further comprising a couch capable of supporting said irradiation target and being placed on an extension of said radiation path.

7. A therapy system using an ion beam according to claim 6, further comprising a positioning information generator for generating information for positioning said couch by using said three-dimensional image information and tomographic information of said irradiation target obtained at a treatment plan for said irradiation target, and a couch movement controller for controlling movement of said couch by using the positioning information.

8. A therapy system using an ion beam according to claim 5, wherein said positioning information generator generates the positioning information by using said three-dimensional image information obtained at a treatment plan.

9. A therapy system using an ion beam according to claim 2, wherein said therapy system further comprises a first annular rotational frame mounted in said rotating gantry, a second annular frame to which said beam delivery unit is fixed, said first annular frame and said second annular frame being arranged in a sandwiching relation to a movement path of said ion beam irradiating unit, and a movable floor capable of being flexural in the circumferential direction of said rotating gantry and being moved in the circumferential direction of said rotating gantry with rotation of said ion beam irradiating unit while being guided by annular guides provided on said first and second annular frames, wherein said ion beam irradiating unit is inserted in a space defined by said movable floor surrounding the space, and said plurality of X-ray detectors detect the X-ray emitted from said X-ray generator in the space.

10. A therapy system using an ion beam according to claim 1, further comprising a detector moving device for moving said plurality of X-ray detectors to a position where the X-ray emitted from said X-ray generator are incident upon said plurality of X-ray detectors.

11. A radiation tomographic image capturing method comprising the steps of:
   rotating a rotating gantry provided with a beam delivery unit for emitting an ion beam for treatment to an irradiation target and a X-ray generator for emitting a X-ray, thereby revolving said radiation generator emitting said X-ray around a couch supporting an irradiation target;

detecting said X-ray having penetrated said irradiation target by a plurality of X-ray detectors mounted to said rotating gantry and revolving around said irradiation target with rotation of said rotating gantry; and forming three-dimensional image information of said irradiation target by using information obtained based on X-ray detection signals outputted respectively from said plurality of X-ray detectors, position information of said X-ray generator emitting the X-ray and position information of said plurality of X-ray detectors outputting the X-ray detection signals.

12. A radiation tomographic image capturing method according to claim 11, further comprising the steps of moving said X-ray generator provided in said beam delivery unit to a position of a radiation path of said ion beam, and emitting said X-ray from said X-ray generator positioned on said radiation path.

13. An X-ray tomographic image capturing method comprising the steps of:

rotating a rotating gantry provided with a beam delivery unit for emitting a ion beam for treatment to an irradiation target and an X-ray generator for emitting an X-ray, thereby revolving said X-ray generator emitting the X-ray around a couch supporting said irradiation target;

detecting the X-ray having penetrated said irradiation target by a plurality of X-ray detectors mounted to said rotating gantry and revolving around said irradiation target with rotation of said rotating gantry; and forming three-dimensional image information of said irradiation target by using information obtained based on X-ray detection signals outputted respectively from said plurality of X-ray detectors, position information of said X-ray generator emitting the X-ray, and position information of said plurality of X-ray detectors outputting the X-ray detection signals.

14. An X-ray tomographic image capturing method according to claim 13, further comprising the steps of moving said X-ray generator provided in said beam delivery unit to a position of a beam path of said ion beam, and emitting the X-ray from said X-ray generator positioned on said beam path.

15. A couch positioning method comprising the steps of:

moving a X-ray generator, which is provided in a beam delivery unit for delivering a chaged particle beam to an irradiation target, to a position of a radiation path of said ion beam;

rotating a rotating gantry provided with said beam delivery unit, thereby revolving said X-ray generator positioned on said radiation path and emitting said X-ray and a plurality of X-ray detectors for detecting said X-ray around a couch supporting said irradiation target;

detecting said X-ray having penetrated said irradiation target by the plurality of X-ray detectors;

forming first three-dimensional image information of said irradiation target by using information obtained based on X-ray detection signals from said plurality of X-ray detectors obtained upon rotation of said rotating gantry, position information of said X-ray generator emitting the X-ray and position information of said plurality of X-ray detectors outputting the X-ray detection signals;

generating information for positioning said couch by using said first three-dimensional image information and second tomographic information of said irradiation target used at a treatment plan for said irradiation target; and moving said couch based on the positioning information.

16. A couch positioning method according to claim 15, wherein said positioning information is generated by using said first three-dimensional image information and said second tomographic information.

17. A couch positioning method according to claim 15, wherein said positioning information is generated by using first two-dimensional image information formed based on said first three-dimensional image information and second two-dimensional image information formed based on said second tomographic information.

18. An ion beam delivery method comprising the steps of:

rotating a rotating gantry provided with a beam delivery unit for delivering an ion beam for treatment to an irradiation target and a X-ray generator for emitting a X-ray, thereby revolving said X-ray generator emitting said X-ray around said irradiation target lying on a couch;

detecting said X-ray having penetrated said irradiation target by a plurality of X-ray detectors mounted to said rotating gantry and revolving around said irradiation target with rotation of said rotating gantry;

positioning said couch based on three-dimensional image information of said irradiation target formed by using information obtained based on X-ray detection signals from said plurality of X-ray detectors obtained upon rotation of said rotating gantry, position information of said X-ray generator emitting the X-ray and position information of said plurality of X-ray detectors outputting the X-ray detection signals, and second tomographic information of said irradiation target used in a treatment plan; and delivering said ion beam from said beam delivery unit to said irradiation target lying on said positioned couch.

19. A couch positioning system comprising:

a rotating gantry;

a beam delivery unit mounted to said rotating gantry and delivering an ion beam for treatment;

an X-ray generator mounted to said rotating gantry and generating a X-ray, said X-ray generator being capable of moving to a position of a radiation path of said ion beam, revolving about a rotation axis of said rotating gantry with rotation of said rotating gantry and emitting X-ray at a plurality of rotation angles of said rotating gantry;

a plurality of X-ray detectors mounted to said rotating gantry, said plurality of X-ray detectors detecting said X-ray emitted from said X-ray generator and outputting X-ray detection signals, and revolving about the rotation axis of said rotating gantry with rotation of said rotating gantry; and a controller for positioning a couch based on three-dimensional image information of an irradiation target formed by using information obtained based on the X-ray detection signals from said plurality of X-ray detectors obtained upon rotation of said rotating gantry, position information of said X-ray generator emitting the X-ray and position information of said plurality of X-ray detectors outputting the X-ray detection signals, and second tomographic information of said irradiation target used at a treatment plan.

20. A therapy system according to claim 1, further comprising an angle sensor for detecting the rotational angle of said rotating gantry, and wherein said image information forming unit determines said position information of the X-ray generator and said position information of the X-ray detectors based on the rotating angle detected by said angle sensor.

21. A therapy system according to claim 5, wherein said positioning information generator uses two-dimensional image information formed based on said three-dimensional image information upon generating said positioning information.

22. A radiation tomographic image capturing method according to claim 11, further comprising the steps of detecting the rotational angle of said rotating gantry, and wherein said position information of the X-ray generator and said position information of the X-ray detectors are determined based on the rotational angle as detected.

23. A radiation tomographic image capturing method according to claim 13, further comprising the steps of detecting the rotational angle of said rotating gantry, and wherein said position information of the X-ray generator and said position information of the X-ray detectors are determined based on the rotational angle as detected.

24. A radiation tomographic image capturing method according to claim 15, further comprising the steps of detecting the rotational angle of said rotating gantry, and wherein said position information of the X-ray generator and said position information of the X-ray detectors are determined based on the rotational angle as detected.

25. An ion beam delivery method according to claim 18, further comprising the steps of detecting the rotational angle of said rotating gantry, and wherein said position information of the X-ray generator and said position information of the X-ray detectors are determined based on the rotational angle as detected.

26. A couch positioning system according to claim 19, further comprising an angle sensor for detecting the rotational angle of said rotating gantry, and wherein said position information of the X-ray generator and said position information of the X-ray detectors is information determined based on the rotational angle of the rotating gantry detected by said angle sensor.

* * * * *